United States Patent [19]
Bright et al.

[11] Patent Number: 5,824,510
[45] Date of Patent: Oct. 20, 1998

[54] MONOCLONAL ANTIBODIES TO HUMAN INFLUX PEPTIDE TRANSPORTER

[75] Inventors: Stuart W. Bright, Indianapolis; Anne H. Dantzig, Crawfordsville; Linda B. Tabas, Carmel, all of Ind.; J. Richard Sportsman, Palo Alto, Calif.

[73] Assignee: Eli Lilly and Company, Indianapolis, Ind.

[21] Appl. No.: 347,760

[22] Filed: Dec. 1, 1994

Related U.S. Application Data

[62] Division of Ser. No. 84,686, Jun. 29, 1993, Pat. No. 5,500,346.

[51] Int. Cl.$^6$ .............................. C07K 16/00; C12P 12/08
[52] U.S. Cl. ................ 435/70.21; 435/69.6; 435/240.27; 530/387.1; 530/387.3; 530/388.2; 530/388.35; 424/152.1
[58] Field of Search ........................... 435/240.27, 70.21, 435/69.6; 530/387.1, 387.3, 388.2, 388.35; 424/152.1

[56] References Cited

U.S. PATENT DOCUMENTS 5,183,756  2/1993  Schlom .............................. 435/240.27

OTHER PUBLICATIONS

Dantzig and Bergin, 1990, Biochimica et Biophysica Acta 1027:211–217.
Dantzig et al., 1992, Biochimica et Biophysica Acta 1112:167–173.
Kramer et al., 1990, Biochimica et Biophysica Acta 1030:41–49.
Kramer et al., 1990, Biochimica et Biophysica Acta 1030:50–59.
Ganapathy and Leibach, 1991, Current Opinion in Cell Biology 3:695–701.
Kramer et al., 1991, International Congress of Chemptherapy, Berlin, F.R.G. Abstract No. 1415.
Bird and Lloyd, 1990, Biochimica et Biophysica Acta 1024:267–270.
Skopicki, et al., 1991, Am. J. Physiol. 261:F670–F678.
Ganapathy, et al., 1981, J. Biol. Chem. 256:118–124.
Said, et al., 1988, Biochim. Biophys. Acta 941:232–240.
Kramer, et al., 1988, Biochim. Biophys. Acta 939:167–172.
Calonge, et al., 1990, Am. J. Physiol. 259:G775–G780.
Shimada and Hoshi, 1986, Jpn. J. Physiol. 36:451–465.
Matthews and Burston, 1984, Clinical Sci. 67:541–549.
Okano, et al., 1986, J. Biol. Chem. 261:14130–14134.
Nakashima, et al., 1984, Biochem. Pharm. 33:3345–3352.
Muranushi, et al., 1989, Pharm. Res. 6:308–312.
Friedman and Amidon, 1989, Pharm. Res. 6:1043–1047.
U.S. application No. 08/013,462, Dantzig et al. filed May 4, 1993.
Friedman and Amidon, 1990, J. Control. Rel. 13:141–146.
Tabas, et al., 1991, 31st Interscience Conference on Antimicrobial Agents and Chemotherapy Abstract No. 164.
Dantzig, et al., 1992, 32nd Interscience Conference on Antimicrobial Agents and Chemotherapy, Anaheim, CA, Abstract No. 1460.
Snyder, et al., 1992, 32nd Interscience Conference on Antimicrobial Agents and Chemotherapy Abstract No. 1461.
Hoshi, 1986, Ion Gradient–Coupled Transport, INSERM Symposium No. 26. Editors: F. Alvarado and C. van Os, Elsevier Science Publishers.
Ganapathy and Leibach, 1983, J. Biol. Chem. 258:14189–14192.
Inui, et al., 1992, J. Pharmacol. Exp. Thera. 260:482–486.
Sezaki and Kimura, 1983, Topics in Pharmaceutical Sciences 133–142.
Okano, et al., 1986, Biochem. Pharmacol. 35:1781–1786.
Bai, et al., 1991, Pharm. Res. 8:593–599.
Kramer, 1987, Biochim. Biophys. Acta 905:65–74.
Miyamoto, et al., 1991, J. Biological Chemistry 266(8):4742–4745.
Kramer, et al., 1988, Biochem. Pharmacol. 37:2427–2435.
Sugawara, M., et al., 1992, J. Pharm. Pharmacol. 44:968–972.
Kramer et al (Abstract) Journal of Chromotography Nov. 23, 1990, 521 (2) pp. 199–210.
Carson et al. Advances in Immunology 1986. vol. 38 p. 275.
Waldmann Science vol. 252 p. 1657 1991.
Harris Tibteun 1993 vol. 11, p. 42.

*Primary Examiner*—Lila Feisee
*Assistant Examiner*—Susan Ungar
*Attorney, Agent, or Firm*—Thomas D. Webster; Thomas G. Plant

[57] ABSTRACT

Monoclonal antibodies which react with the human influx peptide transporter are provided. The human influx peptide transporter-reactive antibodies are useful in the purification of influx peptide transporter and in immunoassays to identify agents taken up into the cell by the human influx peptide transporter mechanism. The monoclonal antibodies are also useful for the detection and treatment of carcinomas derived from the gastrointestinal tract and pancreatic duct.

13 Claims, 2 Drawing Sheets

Figure 2

MONOCLONAL ANTIBODIES TO HUMAN INFLUX PEPTIDE TRANSPORTER

This application is a division of application Ser. No. 08/084,686, filed Jun. 29, 1993, now U.S. Pat. No. 5,500,346.

BACKGROUND OF THE INVENTION

Peptides are transported in and out of human cells by several different transport mechanisms. One influx peptide transporter has been located in the brush border of the epithelial cells of the intestinal mucosa. Properties of this intestinal transporter (hereinafter "influx peptide transporter") have been studied in situ in intestinal mucosa preparations and in vitro with brush border membrane vesicles, isolated enterocytes, and cell culture.

Many different solutes, including small peptides, antibiotics, oral angiotensin converting enzyme (ACE) inhibitors, and oral renin inhibitors are transported into the cytoplasm of the enterocyte by the influx peptide transporter. (e.g., Ganapathy and Leibach, 1991, Curr. Biol. 3:695–701; Okano et al., 1986, J. Biol. Chem. 261:14130–14134; Nakashima et al., 1984, Biochem. Pharm. 33:3345–3352). The influx peptide transporter plays a pivotal role in the absorption of certain oral drugs, including β-lactams and ACE inhibitors. Out of 27 β-lactam antibiotics examined, the influx peptide transporter was able to distinguish between those that are orally absorbed in humans and those that are not (Tabas et al., 1991, 31st Interscience Conference on Antimicrobial Agents and Chemotherapy Abstract No. 164). Moreover, the influx peptide transporter has been demonstrated to transport a number of oral β-lactam antibiotics but not parenteral β-lactam antibiotics in studies using human intestinal Caco-2 cells and rabbit intestinal brush-border membranes (Dantzig et al., 1992, Biochim. Biophys. Acta 1112:167–173; Dantzig et al., 1992, 32nd Interscience Conference on Antimicrobial Agents and Chemotherapy, Anaheim, Calif., Abstract No. 1460; Snyder et al., 1992, 32nd Interscience Conference on Antimicrobial Agents and Chemotherapy Abstract No. 1461; Okano et al., 1986, J. Biol. Chem. 261:14130–14134.) Similar studies have been conducted to examine the ability of the influx peptide transporter to predict which ACE inhibitors are orally absorbed (Friedman and Amidon, 1989, Pharm. Res. 6:1043–1047).

Influx peptide transporter activity has been identified as a 127,000 dalton membrane protein from rabbit intestinal mucosa by photoaffinity labeling methods employing radio-labeled penicillin or a radiolabeled cephalexin analog (Kramer, 1987, Biochim. Biophys. Acta 905:65–74; Kramer et al., 1988, Biochem. Pharmacol. 37:247–2435). A purified 127,000 dalton protein from rabbit intestinal mucosa preparations reconstituted into liposomes resulted in binding and transport activities, and polyclonal antibodies to this putative transporter were prepared (Kramer et al., 1990, Biochim. Biophys. Acta 1030:50–59). Monoclonal antibodies (MAbs) reactive with human influx peptide transporter have not been previously described.

Proteins that are expressed in discrete locations in the body can be used as markers to determine the origin of cells or tissues. For example, carcinoembryonic antigen is a protein situated only in the colon and is used as a marker for colon tumor cells (Shrively, 1985, Crit. Rev. Oncol. Heamatol. 2:355–399). MAbs raised to unique proteins, such as the human influx peptide transporter, can be used to identify tumors and metastases that originate from a tissue that expresses that antigen. This may be done as a diagnostic in the laboratory or may be used in vivo with an imaging agent.

SUMMARY OF THE INVENTION

The present invention provides monoclonal antibodies (MAbs), immunoreactive fragments or recombinants thereof, reactive with human influx peptide transporter, a protein of approximately 120,000 dalton molecular weight.

The present invention also provides a method for preparing a MAb that is reactive with human influx peptide transporter comprising the steps of:
  (a) immunizing an immunocompetent mammal with a source of the human influx peptide transporter;
  (b) fusing lymphocytes of the immunized immunocompetent mammal with myeloma cells to form hybridoma cells;
  (c) screening the hybridoma cells of step (b) for influx peptide transporter reactivity;
  (d) cloning human influx peptide transporter-reactive hybridomas of step (c);
  (e) culturing an influx peptide transporter-reactive hybridoma in a medium to secrete said MAb; and
  (f) recovering the MAb from the culture supernatant.

The present invention further provides a process for preparing a hybridoma that produces a MAb reactive with human influx peptide transporter comprising the steps of:
  (a) immunizing an immunocompetent mammal with the human influx peptide transporter;
  (b) obtaining lymphocytes from the immunized mammal;
  (c) fusing the lymphocytes with myeloma cells to produce hybridoma cells; and
  (d) cloning a hybridoma cell that produces human influx peptide transporter reactive MAbs.

In a further embodiment, the invention provides a method of determining uptake of an agent into a cell by a protein reactive with a human influx peptide transporter-reactive MAb, immunoreactive fragments or recombinants thereof, comprising:
  (a) contacting a human influx peptide transporter-reactive MAb, immunoreactive fragments or recombinants thereof, with a cell that has influx peptide transporter activity, in an aqueous solution under conditions that allow the mAb to bind to the cell;
  (b) adding the agent to be tested to said solution; and
  (c) determining whether transport of the agent into the cell is decreased by the presence of the MAb.

In still another embodiment, the invention provides a method of isolating human influx peptide transporter comprising:
  (a) immobilizing a MAb, immunoreactive fragments or recombinants thereof, reactive with human influx peptide transporter onto a surface;
  (b) contacting said immobilized MAb with a mixture containing human influx peptide transporter under conditions that allow the human influx peptide transporter to bind to the immobilized MAb;
  (c) separating immobilized MAbs that are bound to human influx peptide transporter from said mixture; and
  (d) recovering the human influx peptide transporter by removing the human influx peptide transporter from the MAb.

The invention also provides a method of identifying human influx peptide transporter in a biological sample comprising:

(a) contacting the sample with a MAb, immunoreactive fragments or recombinants thereof, reactive with the human influx peptide transporter;

(b) determining the level of binding of said MAb, immunoreactive fragments or recombinants thereof to the sample; and (c) comparing the amount of the MAb, immunoreactive fragments or recombinants thereof, bound to substances present in the sample to a control sample or to a predetermined base level, so that a binding greater than the control level is indicative of the presence of the human influx peptide transporter in a biological sample.

The invention further provides a method of diagnosing a human gastrointestinal or pancreatic duct carcinoma or metastases therefrom comprising:

(a) obtaining a body sample from a patient;

(b) contacting the body sample material with a MAb reactive with the human influx peptide transporter, immunoreactive fragments or recombinants thereof;

(c) determining the level of binding of said MAb, immunoreactive fragments or recombinants thereof to the body sample material; and (d) determining the level of binding of a MAb reactive with human influx peptide transporter to a body sample known to be free of human gastrointestinal or pancreatic duct carcinoma or metastases therefrom to establish a control;

(e) comparing the amount of the MAb, immunoreactive fragments or recombinants thereof bound to substances present in the body sample in step (c) with the amount of the MAb, immunoreactive fragments or recombinants thereof bound to substances present in the control body sample of step (d), a binding level greater than the control level being indicative of the presence of human gastrointestinal carcinoma or pancreatic duct carcinoma or metastases therefrom.

In another embodiment the invention provides a method for diagnosing the presence of a human gastrointestinal or pancreatic duct carcinoma or metastases therefrom comprising:

(a) administering to a patient MAb reactive with the human influx peptide transporter, immunoreactive fragments or recombinants thereof, conjugated to an imaging marker; and (b) exposing the patient to a means for detecting said imaging marker to identify the presence of the imaging marker in order to detect primary human gastrointestinal or pancreatic duct carcinoma or metastatic sites therefrom in a patient.

In another embodiment, the invention provides a method of treating a patient afflicted with human gastrointestinal carcinoma or metastases therefrom or pancreatic duct carcinoma or metastases therefrom, comprising administering to said patient, a therapeutically effective amount of a MAb, immunoreactive fragments thereof or recombinants thereof reactive with human influx peptide transporter, conjugated to a therapeutic agent.

In another embodiment, the invention provides pharmaceutical compositions comprising MAbs, immunoreactive fragments or recombinants thereof, reactive with human influx peptide transporter.

DETAILED DESCRIPTION OF THE INVENTION

The present invention provides, inter alia, MAbs which react with the human influx peptide transporter, a protein implicated in the transport of various substrates into the cell. The MAbs of this invention are unique in that they inhibit the uptake of substrates by the human influx peptide transporter. MAbs PTC12D8, PTC13G6, and PTC15F11 are reactive with human influx peptide transporter and are illustrative of the MAbs of this invention. The hybridomas that produce PTC12D8, PTC13G6, and PTC15F11, are designated hybridoma PTC12D8, hybridoma PTC13G6, and hybridoma PTC15F11, respectively. Hybridomas PTC12D8, PTC13G6, and PTC15F11 were deposited with the American Tissue Culture Collection (ATCC) Rockville Md., on Feb. 17, 1993, and are available under accession numbers HB 11271, HB 11272, and HB 11273, respectively.

Human influx peptide transporter-reactive MAbs can be prepared by: immunizing an immunocompetent mammal with a protein source containing the human influx peptide transporter; fusing a lymphocyte obtained from the immunized immunocompetent mammal with an appropriate myeloma cell fusion partner to form a hybridoma; screening the resultant hybridomas for influx peptide transporter reactivity; and cloning the influx peptide transporter specific hybridomas by limiting dilution or similar techniques. These and other techniques for the preparation of MAbs are known in the art (see Rice, et al., *Proc. Natl. Acad. Sci. USA*, 79:7862–7865 (1982); Kurokawa, et al., *Nucleic Acids Res.*, 11:3077–3085 (1983); Oi, et al., *Proc. Natl. Acad. Sci. USA*, 80:825–829 (1983); Boss, et al., *Nucleic Acids Res.* 12:3791–3806 (1984); Boulianne, et al., *Nature* 312:643–646 (1984); Cabily, et al., *Proc. Natl. Acad. Sci. USA*, 81:3273–3277 (1984); Kenten, et al., *Proc. Natl. Acad. Sci. USA*, 81:2955–2959 (1984); Liu, et al., *Proc. Natl. Acad. Sci. USA*, 81:5369–5373 (1984); Morrison, et al., *Proc. Natl. Acad. Sci, USA*, 81:6851–6855 (1984); Neuberger, et al., *Nature*, 312:604–608 (1984); Potter, et al., *Proc. Natl. Acad. Sci. USA*, 81:7161–7165 (1984); Neuberger, et al., *Nature*, 314:268–270 (1985); Jones, et al., *Nature* (London), 321:522–525 (1986); Oi, et al., *BioTechniques*, 4:214–221 (1986); Sahagan, et al., *J. Immunol.*, 137:1066–1074 (1986); Sun, et al., *Hybridoma* 5 (Suppl. I):S17–S20 (1986); Sun, et al., *Proc. Natl. Acad. Sci. USA*, 84:214–218 (1987); *Selected Methods In Cellular Immunology*, Mishell and Shiigi, Eds. (W. H. Freeman and Company, New York, N.Y., 1980); and *Methods In Enzymology*, Volume 73 Part B, Langone and Vunakis, Eds., (Academic Press, Inc., New York, N.Y., 1981), all of which are specifically incorporated herein by reference.

Numerous species, including rats, mice, rabbits, and goats, are useful as a source of immunized lymphocytes for the fusion protocols utilized to generate hybridomas. A/J mice are especially preferred as the source of the immune cells for production of human influx peptide transporter specific antibodies.

The MAbs of the present invention can be altered to a chimeric form by substitution, e.g., human constant regions ($F_c$ domains) for mouse constant regions by recombinant DNA techniques known in the art as described in the above cited references. These $F_c$ domains can be of various human isotypes, i.e., $IgG_1$, $IgG_2$, $IgG_4$ or IgM.

In addition, the MAbs of the present invention can be altered to affinity modified forms, avidity modified forms, or both, by altering binding sites or altering the hinge region using recombinant DNA techniques known in the art as exemplified in the above cited references.

The recombinant antibody forms can also be fragmented to produce immunoreactive fragments F(ab')$_2$, F(ab') or F(ab) in the same manner as described above in which the monoclonal antibody of the present invention is fragmented.

Accordingly, as used herein, the expression "recombinant antibodies" collectively includes chimeric/recombinant forms of the monoclonal antibodies of the present invention wherein the Fc domain is substituted for an Fc domain of another species or isotype; affinity modified forms of the monoclonal antibodies of the present invention wherein the binding sites are altered; avidity modified forms of the monoclonal antibodies of the present invention wherein the hinge regions are altered; immunoreactive fragments of the foregoing and combinations thereof.

The MAbs of the present invention can be produced in large quantities by injecting a hybridoma producing monoclonal antibodies of the present invention into the peritoneal cavity of pristane-primed mice, and after an appropriate time (about 1–2 weeks), harvesting ascites fluid from the mice. This method yields a very high titer of homogeneous monoclonal antibody. MAbs are isolated therefrom by methods well known in the art (see Stramignoni, et al., *Intl. J. Cancer* 31:543–552 (1983)). Alternatively, MAbs can be produced by culturing a hybridoma capable of producing MAbs of the present invention in vitro and isolating secreted MAbs from the cell culture medium by methods known in the art (see Colcher, et al., *Proc. Natl. Acad. Sci. USA* 78:3199–3203 (1981)).

To construct hybridomas secreting human influx peptide transporter specific antibodies, a mouse is immunized with a cell or cell preparation which possesses human influx peptide transporter activity. For example, a membrane sample from the Caco-2 cell line, prepared as described in Example 1, can be used as the immunogen to produce the MAbs. The Caco-2 cell line is a human colon adenocarinoma cell line that has been shown to take up antibiotics by an influx peptide transporter (Dantzig and Bergin, 1990, *Biochim. Biophys. Acta* 1027:211–217; Dantzig et al., 1992, *Biochim. Biophys. Acta* 1112: 167–173). Caco-2 cells are available from the American Type Culture Collection (ATCC), 12301 Parklawn Drive, Rockville, Md. 20852-1776, under accession number ATCC HTB37.

Preferably, a final immunization is carried out by administering a Caco-2 cell membrane preparation directly into the peritoneal cavity of the mouse being immunized to enhance the immune response (*J. Immunol. Methods* 70:39–43, 1984), and obtaining splenocytes from the spleen for fusion with myeloma cells. The hybridomas thus obtained are screened by measuring antibody titer in a culture supernatant of the hybridoma. Example 3 of the present disclosure teaches a method for determining whether a hybridoma supernatant reacts with human influx peptide transporter. Antibody-producing hybridomas are then cloned to establish hybridoma cell lines that secrete a MAb specific to the human influx peptide transporter.

MAbs to the human influx peptide transporter are useful in a method for rapidly identifying agents that are transported into human gastrointestinal cells by this mechanism. Transport of an agent by this mechanism is believed to be a predictor of oral bioavailability. Oral bioavailability is a highly desired property of many medications. Determination of the oral bioavailability of a drug at an early stage of development would be particularly advantageous. Presently, drugs are initially evaluated for oral bioavailability in animal models. This process requires selection of only a few compounds whose synthesis must be scaled up to be evaluated in these models. This process is time consuming, laborious, and expensive. Further, there are many examples of chemical agents that are well absorbed in animal models but not absorbed by humans.

The availability of a family of human influx peptide transporter specific antibodies enables the development of numerous assay systems for characterizing therapeutic agents, such as small, hydrophilic compounds, that can be transported into human gastrointestinal or pancreatic duct cells by the human influx peptide transporter. The MAbs of this invention are useful in that they bind the human influx peptide transporter antigen and inhibit human influx peptide transporter function. This feature makes the MAbs of this invention especially useful in assays for determining whether an agent is taken up into the cell by the human influx peptide transporter. As indicated above, uptake of a test agent by this mechanism indicates potential for oral absorption in vivo. Such an assay measures whether uptake into the cell of a particular compound can be decreased or blocked by a MAb of this invention. Decreased or blocked uptake indicates that the test compound is taken up into the cell by the influx peptide transporter.

As described above, the availability of the MAbs of this invention allows the facile preparation the human influx peptide transporter in substantially pure form. After the human influx peptide transporter-reactive MAb has been prepared and purified, the MAb can be immobilized on a surface comprising an insoluble matrix, for example polysaccharides, synthetic polymers, or inorganic materials, to prepare an affinity absorbent. The affinity absorbent can then placed in a chromatography column to prepare an affinity column. As an activated carrier material cyanogen bromide activated Sepharose 4B (Pharmacia), Affigel 10 (Bio-Rad), Affiprep 10 (Bio-Rad), or the like may be used. The affinity absorbent can then be brought into contact with a human influx peptide transporter-containing material, such as a cell membrane preparation of Caco-2 cells. The absorbed human influx peptide transporter is then eluted by an appropriate elution means such as a change in pH, a change in polarity, protein denaturing agent, chaotropic ion or the like. Where the human influx peptide transporter may be inactivated by an eluate, the eluate should be immediately neutralized or dialyzed.

The human influx peptide transporter is located in the brush border of the intestinal mucosa. MAbs to the human influx peptide transporter are also reactive with tissue from the pancreatic duct. The unique location of the human influx peptide transporter provides additional utilities for the MAbs of the present invention. For instance, MAbs, immunoreactive fragments or recombinants thereof, reactive with human influx peptide transporter can be used either alone, or in combination with other antibodies, in in vitro diagnostic assays. For example, body samples of patients can be analyzed using labeled MAbs of this invention for the detection of the antigen with which the MAb react. In vitro diagnostic assays for detection of primary human carcinomas or metastases therefrom by detecting the reactive antigen in body fluids of patients using the monoclonal antibodies of the present invention, immunoreactive fragments or recombinants thereof are described in greater detail below.

The body fluid obtained from a patient is contacted with MAbs of the present invention, immunoreactive fragments or recombinants thereof. A diagnosis is then made by determining the amount of MAb, immunoreactive fragment or recombinant thereof binding to substances present in the body fluid and comparing the amount of MAb bound to the body fluid substances to a predetermined base level. This base level may be determined by the level of binding of a MAb reactive with human influx peptide transporter to a body sample known to be free of human gastrointestinal or pancreatic duct carcinoma or metastases therefrom. The detection of bound MAbs exceeding the base level is indicative of the presence of a human gastrointestinal or pancreatic duct carcinoma or metastases therefrom.

Any body sample suspected of containing the reactive antigen such as blood (serum or plasma), sputum, ascites fluids, pleural effusions, urine and/or biopsy specimens can be used for in vitro diagnostic methods. Serum, plasma, and urine are the more preferred body fluids for use in the practice of the invention.

The amount of antibody bound to substances in the body fluid can be determined by means of immunochemical assays by means such as those described, or example, in Klug, et al., Cancer Res. 44:1048–1053 (1984); Klug, et al., Int. J. Cancer 38:661–669 (1986); Herlyn, et al., J. Clin. Immunol. 2:135–140 (1982); Metzgar, et al., Proc. Natl. Acad. Sci. USA 81:5242–5246 (1984); Papsidero, et al., Cancer Res. 44:4653–4657 (1984); Hayes, et al., J. Clin. Invest. 75:1671–1678 (1985); Killian, et al., Cancer Res. 45:886–891 (1985); Hedin, et al., Proc. Natl. Acad. Sci. USA 80:3470–3474 (1983); Pekary, et al., Clin. Chem. 30:1213–1215 (1984); Bast, et al., New England J. Med. 309:883–887 (1983); and Bellet, et al., Proc. Natl. Acad. Sci. USA 81:3869–3873 (1984), the disclosures of all of which are specifically incorporated herein by reference.

The MAbs of the present invention, immunoreactive fragments or recombinants thereof, can also be used either alone, or in combination with other antibodies in in vivo diagnostic assays such as diagnostic imaging or use with an intraoperative hand-held gamma detecting probe. For example, the MAbs, immunoreactive fragments or recombinants thereof, conjugated to an imaging marker, may be used for the in situ detection of gastrointestinal or pancreatic duct carcinoma lesions. In vivo diagnostic assays for detection of human gastrointestinal or pancreatic duct carcinomas or metastases therefrom using the MAbs of the present invention, are described in more detail below.

In such diagnostic assays, MAbs of the present invention, including immunoreactive fragments or recombinants thereof and an imaging marker are administered to a patient. The marker may be conjugated to the antibody before administration. Alternatively, subsequent administration of the marker or linker conjugated marker after administration of the monoclonal antibody is acceptable. The presence of the imaging marker in the patient is detected by exposing the patient to an appropriate means for detecting the particular marker.

Administration and detection of the antibody-imaging marker conjugate as well as methods of conjugation of the antibody to the imaging marker are accomplished by methods known to those skilled in the art, as described, for example, in Goldenberg, et al., New England J. Med. 298:1384–1388 (1978); Goldenberg, et al., J.A.M.A. 250:630–635 (1983); Goldenberg, et al., Gastroenterol. 84:524–532 (1983); Siccardi, et al., Cancer Res. 46:4817–4822 (1986); Epenetos, et al., Cancer 55:984–987 (1985); Philben, et al., Cancer 57:571–576 (1986); Chiou, et al., Cancer Res. 45:6140–6146 (1985); Hwang, et al., J. Natl. Cancer Inst. 76:849–855 (1986); Colcher, et al., Cancer Res. 43:736–742 (1983); Colcher, et al., Laboratory Research Methods in Biology and Medicine Immunodiagnostics, New York, Alan R. Liss, pp. 215–258 (1983); Keenan, et al., J. Nucl. Med. 25:1197–1203 (1984); Colcher, et al., Cancer Res. 47:1185–1189 (1987); Esteban, et al., Intl. J. Cancer 39:50–59 (1987); Martin, et al., Curr. Surg. 41:193–194 (1984); Martin, et al., Hybridoma 5:S97–S108 (1986); and Martin, et al., Am. J. Surg. 150:672–675 (1985); the disclosures of all of which are specifically incorporated herein by reference.

The dosage of the MAb imaging agent is a pharmaceutically acceptable amount which will vary depending upon the age and weight of the patient, but generally a one time dosage of about 0.1 to 20 milligrams of antibody-marker conjugate is sufficient. A more preferred dosage is about 1.0 to 2.0 milligrams of antibody-marker conjugate.

Imaging markers which can be conjugated to the antibody are known to those skilled in the art and include substances which can be detected by a gamma scanner or hand-held gamma probe, Positron Emission Tomography or the like as described in the references cited above, and substances which can be detected by nuclear magnetic resonance imaging using a nuclear magnetic resonance spectrometer (also described in the references cited above).

Examples of substances which can be detected using a gamma scanner or the like include $^{125}I$, $^{131}I$, $^{123}I$, $^{111}In$, and $^{99m}Tc$. $^{111}In$ and $^{99m}Tc$ are preferred due to their low energy and suitability for long range detection.

An example of a substance which can be detected using a nuclear magnetic resonance spectrometer or the like is the nuclear magnetic spin-resonance isotope gadolinium (Gd).

MAbs to the human influx peptide transporter can be used in vivo because of the unique location of the human influx peptide transporter. The human influx peptide transporter is located in the brush border of the intestinal mucosa and not on the basolateral side of the enterocyte. Because the intestinal mucosa is a tight epithelium which does not permit solutes to readily pass paracellularly (i.e. between cells), and the influx peptide transporter faces the lumen of the intestine, MAbs administered intravenously or intraperitoneally would not be expected to have ready access to the antigen located on the brush border. Because tumor cells do not form a tight epithelium, it is likely that the antigen would be randomly distributed along the cell surface. Consequently, the MAb would localize predominately to tumors expressing the influx peptide transporter.

The MAbs of the present invention, immunoreactive fragments or recombinants thereof, can also be used either alone, or in combination with other antibodies, in immunohistopathology or immunocytochemistry assays for the diagnosis of human carcinomas or metastases therefrom. For example, the MAbs of the present invention, are added to a slide containing a 5 micron section of a biopsy specimen (for immunohistochemistry) or cells (for immunocytochemistry) from body fluid (such as a pleural effusion, ascites sputum, or vaginal fluid). A series of linkers (e.g., biotinylated horse anti-mouse IgG followed by avidin DH:biotinylated horseradish peroxidase complex) and dyes (e.g. diaminobenzidine) are then added to the slides to detect binding of the monoclonal antibody, immunoreactive fragment or recombinant thereof to carcinoma cells in the biopsy or body fluid by a color reaction, i.e., carcinoma cells will look reddish-brown, while normal and benign cells will look blue (the background stain). Other detection methods may be used with alternate linkers, dyes, and subsequent color reactions (see, for example, Sternberger, L. A., *Immunocytochemistry*, New York, John Wiley & Sons, Second Edition, pp. 82–169 (1979)). By this method: (a) carcinoma cells can be detected in biopsy specimens and body fluids as an adjunct to making a diagnosis of cancer, and (b) a differential diagnosis can be made. For example, MAb PTC13G6 has been shown to bind human tumor cell lines derived from the colon but not to human tumor cell lines derived from human blood and brain (see FIG. 1). Thus, detection of binding of MAbs of the present invention (including immunoreactive fragments or recombinants thereof) would indicate a gastrointestinal origin of the primary carcinoma.

The use of immunohistochemistry and immunocytochemistry assays for the diagnosis of cancer or to make differential diagnoses are accomplished by methods known in the art, as described, for example, in Nuti, et al., *Intl. J. Cancer* 29:539–545 (1982); Stramignoni, et al., *Intl. J. Cancer* 31:543–552 (1983); Szpak, et al., *Acta Cytologica* 28:356–367 (1984); Johnston, et al., *Cancer Res.* 45:1894–1900 (1985); Szpak, et al., *Am. J. Path.* 122:252–260 (1986); Thor, et al., *J. Natl. Cancer Inst.* 76:995–1006 (1986); Martin, et al., *Am. J. Clin. Path.* 86:10–18 (1986); Nuti, et al., *Intl. J. Cancer* 37:493–498 (1986); Johnson, et al., *Cancer Res.* 46:850–857 (1986); Thor, et al., *Cancer Res.* 46:3118–3124 (1986); Obuchi, et al., *Intl. J. Cancer* 38:643–650 (1986); Johnston, et al., *Cancer Res.* 46:6462–6470 (1986); and Thor, et al., *Cancer Res.* 47:505–512 (1987), the disclosures of all of which are specifically incorporated herein by reference.

Labeling of the MAb for use in such assays is carried out by conventional procedures. For the radioimmunoassay, a radioisotope such as $^{125}I$ is used. For the enzyme immunoassay, conventional enzymes such as peroxidase or β-galactosidase are used. For the fluorescent immunoassay, conventional chromophores can be used as markers. These assay methods, and modifications thereof, are well known in the art. Assay systems are discussed further in *Methods in Enzymology*, Vol. 73, Part B, supra, the contents of which are herein incorporated by reference. Section II of *Methods in Enzymology*, Vol. 73, Part B, supra, discusses labeling of antibodies and antigens, while Section IV, discusses immunoassay methods.

MAbs to the human influx peptide transporter are also useful in in vivo treatment of human gastrointestinal carcinomas or human pancreatic duct carcinomas or metastases therefrom. In vivo treatment of human gastrointestinal carcinomas or metastases therefrom using MAbs of the present invention, immunoreactive fragments or recombinants thereof is described in greater detail below.

A pharmaceutically effective amount of MAbs of the present invention, immunoreactive fragments or recombinants thereof unconjugated or conjugated to a therapeutic agent is administered to a patient. Methods of preparing and administering the monoclonal antibody-therapeutic agent conjugate as well as suitable dosages will depend on the age and weight of the patient and the therapeutic agent employed and are known to or readily determined by those skilled in the art. Representative protocols are described in the references cited below.

Examples of the monoclonal antibody-therapeutic agent conjugates which can be used in therapy include antibodies coupled to radionuclides, such as $^{131}I$, $^{90}Y$, $^{105}Rh$, $^{47}Sc$, $^{67}Cu$, $^{212}Bi$, and $^{211}At$, as described, for example by Goldenberg, et al., *Cancer Res.* 41:4354–4360 (1981); Carrasquillo, et al., *Cancer Treat. Rep.* 68:317–328 (1984); Zalcberg, et al., *J. Natl. Cancer Inst.* 72:697–704 (1984); Jones, et al., *Int. J. Cancer* 35:715–720 (1985); Lange, et al., *Surgery* 98:143–150 (1985); Kaltovich, et al., *J. Nucl. Med.* 27:897 (1986); Order, et al., Int. J. Radiother. Oncol. Biol. Phys. 8:259–261 (1982); Courtenay-Luck, et al., *Lancet* 1:1441–1443 (1984) and Ettinger, et al., *Cancer Treat. Rep.* 66:289–297 (1982), the disclosure of all of which are specifically incorporated herein by reference. Antibodies coupled to drugs or biological response modifiers such as methotrexate, adriamycin, and interferon as described, for example, in Chabner, et al., *Cancer Principles and Practice of Oncology*, Philadelphia, Pa., J. B. Lippincott Co. Vol. 1, pp. 290–328 (1985); Oldham, et al., *Cancer Principles and Practice of Oncology*, Philadelphia, Pa. J. B. Lippincott Co., Vol. 2, pp. 2223–2245 (1985); Deguchi, et al., *Cancer Res.* 46:3751–3755 (1986); Deguchi, et al., *Fed. Proc.* 44:1684 (1985); Embleton, et al., *Br. J. Cancer* 49:559–565 (1984) and Pimm, et al., *Cancer Immunol. Immunother.* 12:125–134 (1982), the disclosure of all of which are specifically incorporated herein by reference. Antibodies coupled to toxins, as described, for example, in Uhr, et al., *Monoclonal Antibodies and Cancer*, Academic Press, Inc., pp. 85–98 (1983), Vitetta, et al., *Science* 219:664–650 (1983), the disclosure of all of which are specifically incorporated herein by reference. Heterobifunctional antibodies for example, antibodies coupled or combined with another antibody so that the complex binds both to the carcinoma and effector cells, e.g., killer cells such as lymphokine activated killer (hereinafter "LAK") (see Rosenberg, et al., *Science* 223:1412–1415 (1984) or T cells, as described, for example, in Perez, et al., *J. Exper. Med.* 163:166–178 (1986); and Lau, et al., *Proc. Natl. Acad. Sci. USA* 82:8648–8652 (1985); the disclosures of both of which are specifically incorporated herein by reference; and native, i.e., non-conjugated or non-complexed, antibody, as described in, for example, in Shiloni, et al., *J. Immunol.* 138:1992–1998 (1987); Eisenthal, et al., *Cancer Res.* 47:2771–2776 (1987); Honsik, C. J. et al., *Proc. Natl. Acad. Sci. USA* 83:7893–7897; Herlyn, et al., *Proc. Natl. Acad. Sci. USA* 79:4761–4765 (1982); Schulz, et al., *Proc. Natl. Acad. Sci. USA* 80:5407–5411 (1983); Capone, et al., *Proc. Natl. Acad. Sci. USA* 80:Z328–7332 (1983); Sears, et al., *Cancer Res.* 45:5910–5913 (1985); Nepom, et al., *Proc. Natl. Acad. Sci. USA* 81:2864–2867 (1984); Koprowski, et al., *Proc. Natl. Acad. Sci. USA* 81:216–219 (1984); and Houghton, et al., *Proc. Natl. Acad. Sci. USA* 82:1242–1246 (1985) all of which are specifically incorporated herein by reference.

The monoclonal antibody-therapeutic agent conjugate is delivered to the gastrointestinal carcinoma site where binding occurs, thereby directly exposing the carcinoma tissue to the therapeutic agent. Previous therapeutic studies using high doses of monoclonal antibodies such as 17-1A, which is reactive with normal gastrointestinal epithelium, have resulted in no apparent toxicity (see Sears, et al., *J. Biol. Resp. Mod.* 3:138–150 (1984). Furthermore, even where toxicity results in damage, normal gastrointestinal epithelium has been shown to regenerate after such exposure while carcinoma cells do not regenerate.

A pharmaceutical composition comprising the MAbs, immunoreactive fragments or recombinants thereof, of the present invention in a pharmaceutically acceptable, non-toxic, sterile carrier such as physiological saline, non-toxic buffers, and the like, now also becomes possible. The amount of said MAbs in the pharmaceutical composition should be sufficient to achieve effective binding with the antigen against which said MAbs have specific affinity or neutralizing reactivity. The pharmaceutical composition may be administered by single or multiple dosage with other adjuvants or additives, if necessary, in any suitable manner to the host in need of said MAbs.

MAbs to the human influx peptide transporter are also useful as tools in the cloning of cDNA for the influx peptide transporter and related genes. As described in Example 7, these MAbs can be used to detect the expression of cDNA encoding the human influx peptide transporter. The MAbs of this invention may also be used to detect expression of proteins with the same or closely related antigen as the human influx peptide transporter. Thus, the MAbs of this invention have an additional utility in that they are useful in the identification of DNA encoding the human influx peptide transporter or related genes. Techniques for DNA cloning and expression thereof are described by Maniatis, et al. *Molecular Cloning: A Laboratory Manual,* Cold Spring Harbor Press, Cold Spring Harbor Laboratory, Cold Spring Harbor, N.Y. (1989).

The MAbs of this invention can also be used for detecting proteins which possess the same or a closely related antigen to the influx peptide transporter. Also, as indicated in Example 5, the MAbs of this invention are useful in providing clinical information regarding the tissue distribution of the influx peptide transporter.

The Examples which follow are intended to further illustrate the present invention and are not to be interpreted as limiting on the scope thereof.

EXAMPLE 1

Preparation of Caco-2 Membranes

Caco-2 cells are available from the American Type Culture Collection (ATCC), 12301 Parklawn Drive Rockville, Md. 20852-1776, under accession number ATCC HTB37. Caco-2 cells were grown in Dulbecco's Modified Eagle medium (Gibco, Grand Island, N.Y.) containing 10% fetal calf serum (Hyclone) and 1% Minimal Essential Media non-essential amino acid solution (Gibco) as previously described by Dantzig et al., 1990, *Biochim. Biophys. Acta* 1027: 211–217, the entire contents of which are incorporated herein by reference.

Partially purified Caco-2 membranes were prepared from a 2 to 3 week post-confluent culture of Caco-2 cells as follows. A total of approximately $4 \times 10^8$ cells (grown as described above) were disrupted using a glass Dounce homogenizer. Membranes were collected by differential centrifugation (Lever, 1977, *J. Biol. Chem.* 252:1990–1997). After homogenization in 0.25M sucrose, 0.1M Tris, pH 7.5, 0.2 mM $CaCl_2$, 0.04 mg/ml bacitracin, 2 µg/ml aprotinin and 0.02 mM phenylmethanesulfonylfluoride, the sample was centrifuged at 3,000×g for 10 minutes. Supernatants were layered over a 35% sucrose gradient and centrifuged at 16,000×g for 1 hour. The interface was removed, and centrifuged at 100,000×g for 60 minutes. Membranes were enriched approximately 6-fold in alkaline phosphatase activity measured with an alkaline phosphatase assay kit (Sigma Chemical Co., St. Louis, Mo., Procedure No. DG 1245).

EXAMPLE 2

Preparation of MAbs Against Human Influx Peptide Transporter

A) Immunization

Mice (A/J, Jackson Laboratory, Bar Harbor, Me.) were injected subcutaneously three times with a 140–250 µg protein sample of the Caco-2 membranes (prepared as described in Example 1B), over a 6 week period. The mice were boosted with an injection of 180 µg protein three days prior to sacrifice. On day 94 blood was removed from the mice to yield 400 µl of antiserum.

B) Preparation of Myelomas

On day 94 the mice were sacrificed and their spleens were removed. Activated lymphocytes were isolated and fused with mouse myeloma (X63/Ag8.653, ATCC, Rockville, Md.) according to standard hybridoma methods. See generally, Starling et al., *Cancer Immunol. Immunother.* 28:171 (1989).

C) Growth of the Hybridomas

After the fusion, hybridomas were diluted and grown for 23 days in Eagle's medium (Gibco) supplemented with hypoxanthine/aminopterin/thymidine selection medium (Sigma Chemical Co.) and gentamicin (25 µg/ml; Sigma) in 96-well microtiter dishes.

EXAMPLE 3

Hybridoma Screening

After 2–3 weeks, approximately 1200 hybridomas were screened for the ability to block the accumulation of 1 mM cephalexin into two to three week post-confluent Caco-2 cells in substantial accordance with the assay described by Dantzig et al., 1990, *Biochim. Biophys, Acta* 1027:211–217. Cephalexin is available from Eli Lilly and Company, Indianapolis, Ind. Briefly, supernatants from these hybridomas were pooled by rows and by columns yielding 320 pooled supernatants. Confluent Caco-2 cells were washed with Earle's balanced salt solution (Gibco) containing 25 mM HEPES, pH 7.4 (EBSS) and incubated 45 minutes at 37° C., and then the EBSS was removed by aspiration. 300 µl samples of each pooled supernatant were added to the cells and incubated at 37° C. for 2 hours. Uptake of 1 mM [$^{14}$C]cephalexin (labeled as described by Dantzig et al., *Biochem. Biophys. Res. Commun.* 155:1082–1087) was measured at 37° C. for 1 hour in sodium-free Earle's balanced salt solution containing 120 mM choline chloride, 25 mM MES (2-(N-morpholino)-ethanesulfonic acid), pH 6.0 (sodium-free, Trans-EBSS). Subsequently cells were washed three times with ice cold EBSS, pH 7.4. Microtiter dishes were screened for radioactivity using an AMBIS (Radioanalytical Imaging System, Model 100, Ambis, San Diego, Calif.). Using this methodology, 24 pooled supernatants were identified as reducing uptake.

Samples of individual supernatants (800 µl) from the rows and columns that corresponded to the pooled supernatants that reduced [$^{14}$C]cephalexin uptake were subsequently screened for inhibition of [$^{14}$C]cephalexin uptake. The supernatants of three hybridomas reduced uptake using the same protocol described above for the pooled supernatants. Two inhibited uptake by 60–90% in the initial screen (Hybridoma PTC12D8 and Hybridoma PTC13G6) and a third blocked uptake by 20% (Hybridoma MAb PTC15F11).

These hybridomas were subcloned by limiting cell dilutions followed by the fluorescence activated cell sorting technique reported by Marder et al., 1990, *Cytometry,* 11: 498–505. The isotypes of the MAbs of this invention were determined by a commercially available isotyping kit ("Mouse Typer", Bio-Rad Labs, Richmond, Calif. 94804). MAbs PTC12D8 and PTC13G6 were found to be an $IgG_1$ (Kappa) isotype. MAb PTC15F11 was found to be an IgM (Kappa) isotype.

EXAMPLE 4

Characterization of the Antigen

A. Separation of Membrane Proteins and Immunoblot Analysis

Ten to fourteen day post-confluent Caco-2 cells were grown in a T-75 flask in Dulbecco's Modified Eagle medium (Gibco) at 37° C. After aspirating off the growth media, 5 ml of phosphate-buffered saline, pH 7.4 (PBS) were added and cells were scraped and removed. The cells were collected by centrifugation and then resuspended in 1 ml phosphate buffered saline (PBS) and placed in 1.5 ml microfuge tube. Cells were collected in a microfuge. Buffer was removed and cells were resuspended in 200 µl 0.01M Tris-HCl (pH 7.4) 1% Triton X-100 and placed on ice for 20 minutes. Cells were drawn in and out of a syringe three times with a 25 gauge needle. The lysate was centrifuged at 12,000×g for 5 minutes. The supernatant containing crude membranes was removed and the protein content was determined. An aliquot of the membrane preparation containing 100 µg of protein was mixed 1:4 v/v with a 9.2% sodium dodecyl sulfate (SDS) and then 100 µl of bromophenol blue solutions was added. A sample of these membrane proteins was separated by 8–16% SDS-polyacrylamide gel electrophoresis (SDS-PAGE) with a running buffer of 0.25M Tris, 1.92M glycine, 1% w/v SDS at 45 volts for approximately 14 hours. The gel was electroblotted onto nitrocellulose paper in 50 mM phosphate, pH 7.4, at 1.6 amps for 3 hours; the paper (blot) was blocked with 3% bovine serum albumin and 15 mM NaCl, 1 mM EDTA, and 0.1% Triton X-100 in Tris-HCl, pH 7.5 (rinse buffer) at 25° C. The blot was washed twice with rinse buffer. The blot was incubated in rinse buffer containing purified mouse anti-human peptide transporter MAb (MAbs PTC13G6, PTC12D8, or MAb PTC15F11; 20 µg/ml) and incubated for 1 hour at 25° C. The blot was subsequently washed three times with rinse buffer, and incubated in rinse buffer containing 50 ng/ml goat [$^{125}$I] antimouse immunoglobulin G (0.3 µCi/ml) or 32 ng/ml goat [$^{125}$I] antimouse immunoglobulin M for 30 minutes at 25° C. The blot was washed four times, air dried, and exposed to film with two intensifying screens at −70° C. overnight. MAbs PTC13G6 and PTC12D8 detected the presence of a single ~120 kilodalton protein. MAb PTC15F11 detected no protein band.

Although MAb PTC15F11 detected no band, the MAb does react with the peptide transporter. The specificity of MAb PTC15F11 is conformation dependent. Protein conformation is altered by electrophoresis and electroblotting. MAb PTC15F11's specificity for the influx peptide transporter was measured as follows. An aliquot of the Caco-2 membrane preparation containing 30 µg of protein was added to a mixture containing: 50 µl of agarose conjugated to goat anti-mouse antibody (Fc specific for IgM, Sigma Chemical, St. Louis, Mo.), 4 µg of PTC15F11, 300 µl of PBS (pH 7.4) and 2% bovine serum albumin (BSA). The membrane protein preparation had been precleared by preincubation with the goat anti-mouse immunoglobulin agarose conjugate and then using the supernatant. This is done to remove any proteins that may bind non-specifically to the agarose or goat anti-mouse immunoglobulin.

The immunoprecipitation mixture was rocked gently at 4° C. for 16 hours. The agarose pellet was washed 3 times in PBS by centrifugation. The pellet was resuspended in sodium dodecyl sulfate (SDS) sample buffer (0.125M Tris-HCl, pH 6.8, 4% SDS, 20% glycerol, 5% 2-mercaptoethanol) then boiled for 5 minutes. An aliquot of the supernatant was loaded onto an 8–16% SDS-polyacrylamide gel. The proteins were separated by electrophoresis with a running buffer of 0.025M Tris, pH 8.3, 0.192 glycine, 0.1% SDS at 30 mA for 90 minutes.

The gel was electroblotted onto nitrocellulose paper in 12 mM Tris, 96 mM glycine, pH 8.3 with 20% methanol at 30 volts for 90 minutes. The paper was blocked in 2% BSA in 0.02M Tris, 0.15M NaCl, pH 7.4 (Tris-buffered saline, TBS) for 16 hours at 4° C. The blot was then incubated in TBS containing 0.2% BSA (incubation buffer) and MAb PTC13G6 (20 µg/mL) for 2 hours at 25° C. The blot was washed 3 times with TBS containing 1 mM EDTA and 0.1% Triton X-100 (rinse buffer). The blot was incubated in incubation buffer containing goat anti-mouse IgG-horseradish peroxidase (Sigma Chemical) at a 1:1000 dilution for 1 hour at 25° C. The blot was washed 3 times with rinse buffer and 1 time with TBS. Tetramethylbenzidine substrate (TMB; Kirkgaard and Perry Labs, Gaitherburg, Md.) was added to the blot and allowed to react for 15 minutes at 25° C. The TMB solution was removed and deionized water was added immediately to stop the reaction. MAb PTC13G6 detected the presence of a 120 kilodalton protein following immunoprecipitation with MAb PTC15F11.

B. Purification of MAbs

MAbs PTC12D8 and PTC13G6 were purified as follows. Crude ascites fluid containing either PTC12D8 or PTC13G6 was prepared according to standard methods (Campbell, 1986, *Monoclonal Antibody Technology* p. 230). The ascites fluid was diluted 1:1 with glycine-OH buffer (1.45M, pH 8.9) and added to a Sepharose-Protein A column (5 ml bed volume). The column was washed with 10 bed volumes of the glycine buffer. The MAb was eluted with 0.04M sodium citrate, pH 3.2. The eluted fraction was neutralized by adding 0.5M sodium phosphate buffer, pH 7.7, at a ratio of 1:10. The MAb prep was dialyzed against phosphate buffered saline (PBS), pH 7.2 and read at 280 nm to determine concentration.

MAb PTC15F11 was semipurified by precipitating the MAb from crude ascites with 18% sodium sulfate, and then dialyzed against PBS. The semipurified preparation was injected into a Zorbax GF-450 size exclusion column (DuPont, Wilmington, Del. 1989). Fractions obtained from the largest isolated peak were pooled, and read at 280 nm to determine concentration.

EXAMPLE 5

Immunohistochemistry

Frozen tissue specimens of normal human tissue (5µ sections) were dried and fixed with formalin in accordance with the method of Wilson et al., 1990, *Cancer Research* 50:3124–3130. Specimens were incubated with 5 µg/ml of MAb PTC13G6 followed by incubation with a secondary goat anti-mouse IgG antibody conjugated to horseradish peroxidase. An irrelevant, isotype matched antibody, was used for comparison. Analysis revealed that MAb PTC13G6 was strongly positive to human tissues along the gastrointestinal tract (jejunum, duodenum, ileum, and colon) and to the ducts of the pancreas, and negative to kidney, lung, liver, brain, adrenal gland, and skin. Furthermore, the antigen was expressed on the intestinal (apical) side of the gastrointestinal epithelium. It is noteworthy that the antigen was absent in kidney tissues since a peptide transporter is present there (Miyamoto et al., 1985, *Biochem. Biophys. Res. Commun.* 132:946–953; Skopicki et al., 1991, *Am. J. Physiol.* 261:F670–F678.

EXAMPLE 6

Immunoblot Analysis

Figure 1:
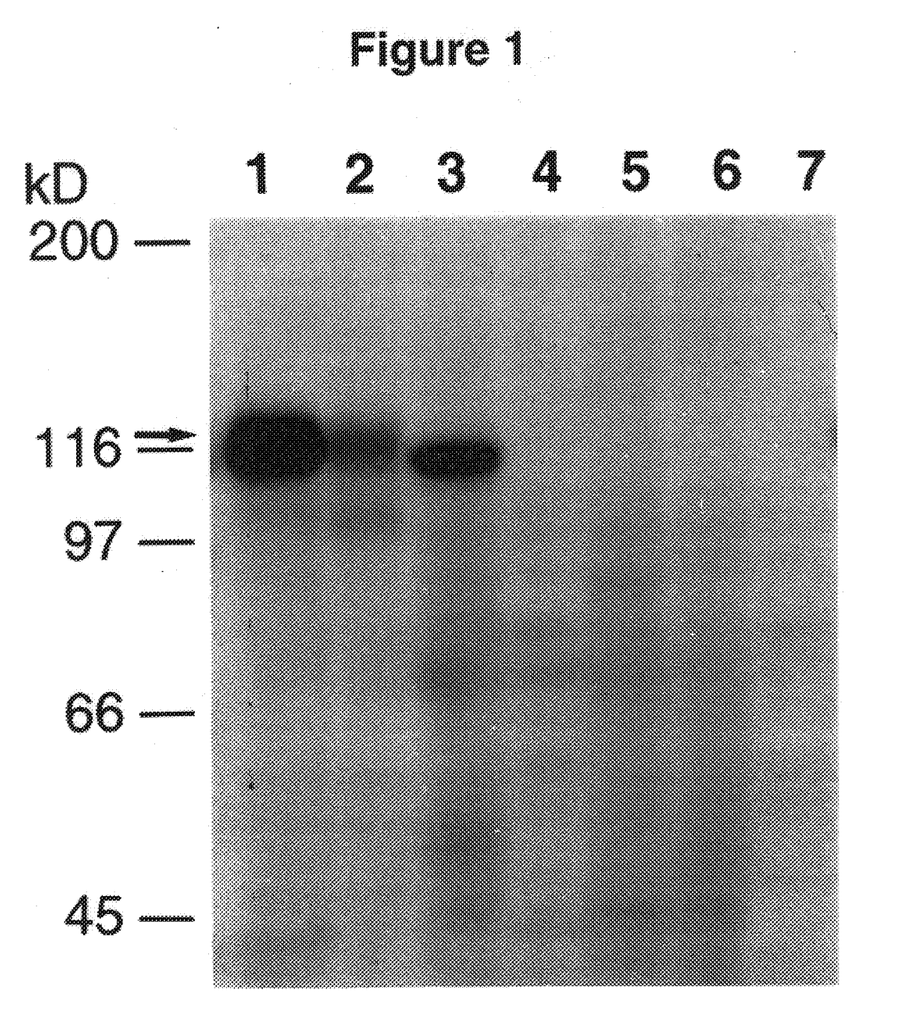
FIG. 1 is an immunoblot analysis of membranes from human tumor cell lines with MAb PTC13G6 performed as described in Example 6. Lane 1 is Caco-2 cells (human colon cells); lane 2 is HT-29 cells (human colon cells); lane 3 is COLO 320 cells (human colon cells); lane 4 CCRF-CEM cells (human lymphoblast cells); lane 5 is IM-9 cells (human lymphoblast cells); lane 6 is SK-N-MC (human neuroblastoma cells); lane 7 is U-373 cells (human glioblastoma cells). The arrow in FIG. 1 indicates the band for the human influx peptide transporter, an approximately 120,000 dalton protein.

Membrane proteins of a variety of human tumor cell lines were prepared in substantial accordance with the method described in Example 1. Membrane proteins were separated by 8% sodium dodecyl sulfate polyacrylamide gel electrophoresis (SDS-PAGE). The gel was electroblotted onto nitrocellulose paper, blocked with 3% bovine serum albumin and 0.1% Triton X-100, 150 mM NaCl, 1 mM EDTA, 0.01M Tris-HCl, pH 7.5, and reacted with 20 $\mu$g/ml MAb PTC13G6 followed by incubation with goat anti-mouse [$^{125}$I] immunoglobulin G (0.3 $\mu$Ci/ml). The results are shown in FIG. 1. Lane 1 is Caco-2 cells (human colon); lane 2 is HT-29 cells (human colon); lane 3 is COLO 320 cells (human colon); lane 4 CCRF-CEM cells (human lymphoblast); lane 5 is IM-9 cells (human lymphoblast cells); lane 6 is SK-N-MC (human neuroblastoma cells); lane 7 is U-373 cells (human glioblastoma cells). The arrow in FIG. 1 indicates the band for the human influx peptide transporter, an approximately 120,000 dalton protein. As indicated by FIG. 1, MAb PTC13G6 detected the presence of the human influx peptide transporter in human colon tumor cell lines. MAb PTC13G6 did not detect the presence of the human influx peptide transporter in human tumor cell lines originating from the blood or the brain.

EXAMPLE 7

Inhibition of Cephalexin Uptake

Figure 2:
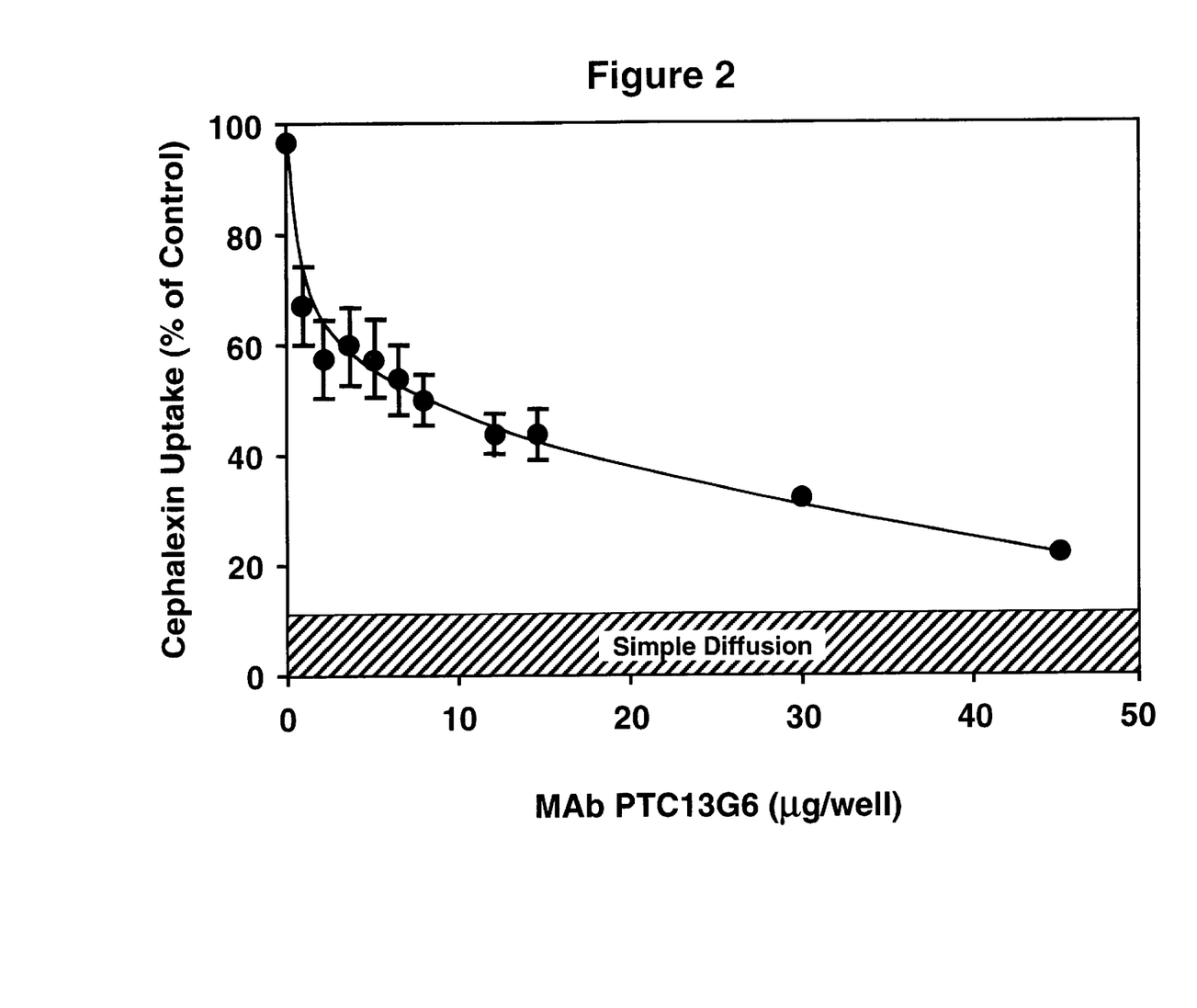
FIG. 2 shows the effect of cephalexin uptake by Caco-2 cells in the presence or absence of MAb PTC13G6.

The effect of preincubation of Caco-2 cells with increasing concentrations of MAb PTC13G6 on 1 mM [$^{14}$C] cephalexin uptake was measured as follows. Growth medium was removed from 14-day old post-confluent Caco-2 cells grown in Costar multiwell dishes (24 wells) and replaced with 1.5 ml of diluted supernatant from hybridoma PTC13G6. Cells were incubated for 2 to 2.5 hours, rinsed once with 1 ml of 37° C. Trans-EBSS, pH 6.0. After aspiration, the uptake rate of 1 mM [$^{14}$C]cephalexin in Trans-EBSS, pH 6.0 was measured over a 4 minute time course in accordance with the method described by Dantzig, 1990, supra. The results of this assay are shown in FIG. 2. The shaded portion of FIG. 2 represents uptake due to simple diffusion which was estimated by the portion that could not be inhibited by the presence of 50 mM of the dipeptide, glycyl-L-proline.

EXAMPLE 8

Expression Cloning

Plasmid pPSJ179 is approximately 8500 base pairs in length and contains DNA encoding the influx peptide transporter from Caco-2 cells. Plasmid pPSJ179 was constructed by cloning a 3.4 kilobase pair XbaI-HindIII cDNA restriction enzyme fragment that comprises the influx peptide transporter-encoding DNA into the commercially available vector pRc/RSV (Invitrogen). The 3.4 kilobase pair XbaI-HindIII cDNA restriction enzyme fragment was identified with the MAb PTC13G6 by expression cloning essentially as described by Maniatis et al., 1989. Plasmid pPSJ179 contains the ampicillin resistance gene for selection in *Escherichia coli,* neomycin resistance gene for selection in eukaryotic cells and the influx peptide transporter gene positioned for expression from the Rous Sarcoma virus (RSV) promoter. Plasmid pPSJ179 can be isolated from *Escherichia coli* K12 DH5$\alpha$/pPSJ179 using a standard alkaline-SDS procedure (Maniatis et al., 1989). *Escherichia coli* K12 DH5$\alpha$/pPSJ179 was deposited with the Northern Regional Research Laboratories (NRRL) in Peoria, Ill. 61604, on Jan. 21, 1993, and is available under accession number NRRL B-21041.

Chinese hamster ovary cells (CHO-K1, ATCC CCL 61) were transfected with plasmid pPSJ179 using a calcium precipitation protocol described in the Stratagene human transfection kit (Stratagene Catalog #200285). The calcium precipitation protocol transfection method was carried out as follows. Subconfluent CHO-K1 cells (100 mm culture dish, 1-day post plating) were incubated for 24 hours in a 3% $CO_2$ incubator at 37° C. with 20 $\mu$g of a calcium-precipitated DNA sample. The DNA sample was either plasmid pPSJ179 or, as control, plasmid pRc/RSV, the vector used to construct pPSJ179. Subsequently, the cells were grown for 3 days in F12 medium containing 10% fetal bovine serum (Hyclone Laboratories Inc., Logan, Utah 84321). Afterwards, the medium was replaced with growth medium containing the selection agent, G-418 sulfate at 300 $\mu$g/ml (Gibco, Grand Island, N.Y.) and cells were grown in a 5% $CO_2$ incubator at 37° C. for 13 days. Colonies which were selected for further study were grown for selected time periods in the selection medium in 24 well plates at 37° C. in a 5% $CO_2$ incubator. Transfectants were evaluated for expression of the influx peptide transporter using an enzyme linked immunosorbent assay (ELISA) and MAb PTC13G6. The ELISA was performed as follows. The medium was removed from the 24 well plates that contained monolayers of the CHO-K1 cells. Two ml of TBS-BLOTTO (TBS (0.02M Tris, 0.14M NaCl, pH 7.4) containing nonfat dried milk (0.5%)) were added to each well and the plates were incubated at room temperature for 30 minutes. Twenty $\mu$g/ml of MAb PTC13G6, 15 $\mu$g/ml of a control monoclonal antibody, or buffer alone, were added to each well in a volume of 250 $\mu$l. The plate was incubated at room temperature for 45 minutes. Following incubation, the cells were washed one time with TBS-BLOTTO. Goat anti-mouse IgG-horseradish peroxidase (Jackson Immunoresearch Laboratories, West Grove, Pa.) diluted 1:2000 was added to each well in a volume of 250 $\mu$l. The plates were incubated at room temperature for 45 minutes. Following incubation, the samples were washed three times with TBS-BLOTTO and then washed two times with TBS. Tetramethyl-benzidine substrate (TMB) (Kirkegaard and Perry Labs, Gaithersburg, Md.) was added to each well in a volume of 250 $\mu$l. The samples were incubated at room temperature for 20 minutes. One molar $H_3PO_4$ was then added to each well in a volume of 250 $\mu$l to stop the reaction. A 100 ml aliquot was transferred from each well of the 24 well plate to a single well on a 96 well plate. Absorbance readings were read at 450 nm on a spectrophotometer. Higher absorbance readings indicate binding of the MAb, and therefore, presence of the influx peptide transporter antigen. Clones that expressed higher levels of the influx peptide transporter antigen than the control were selected for transport studies.

EXAMPLE 9

[$^{14}$C]cephalexin Uptake

Clones selected by ELISA in Example 8 were evaluated for the uptake of 1 mM [$^{14}$C]cephalexin. The transfected CHO-K1 cells (~2.4×10$^4$ cells per well) were grown for 13–17 days in a Costar 24-well plate as described above. Confluent cells were washed with Earle's balanced salt solution (Gibco) containing 25 mM HEPES, pH 7.4 (Trans-EBSS) and incubated 45 minutes at 37° C., and then the Trans-EBSS was removed by aspiration. The cells were incubated in the presence of 1 mM [$^{14}$C]cephalexin in sodium-free Earle's balanced salt solution containing 120 mM choline chloride, 25 mM MES, pH 6.0 (sodium-free, Trans-EBSS) at 37° C. for 2 hours. Subsequently, cells were washed with ice cold Trans-EBSS, pH 7.4, lysed in 0.2N NaOH, and an aliquot was removed for scintillation counting.

A representative transfectant (Clone 9) displayed significantly higher uptake of [$^{14}$C]cephalexin than the control. A further study indicated that uptake of 1 mM cephalexin by this transfectant was inhibited by the presence of 15 mM of bestatin, a dipeptide that is known to compete for uptake by the influx peptide transporter (Saito et al., 1993, *Biochem. Pharmacol.* 45(3):776–779 and Inui et al., 1992, *J. Pharmacol. Exp. Therap.* 260:482–486), or 25 mM unlabelled cephalexin. Coincubation of the cells with 1 mM [$^{14}$C] cephalexin and bestatin or unlabelled cephalexin decreased drug uptake in the representative transfectant (Clone 9) to the level of the control cells. Moreover, transport of 1 mM [$^{14}$C]cephalexin by the control cells was not inhibited significantly by bestatin or by cephalexin. The results of these studies are provided in Table 1.

TABLE 1

| Sample | [$^{14}$C]-Cephalexin Uptake (nmol/mg total cell protein) |
| --- | --- |
| Clone 9 | 1.11 ± 0.08 |
| Clone 9 + bestatin | 0.42 ± 0.08 |
| Clone 9 + cephalexin | 0.35 ± 0.09 |
| Control | 0.55 ± 0.09 |
| Control + bestatin | 0.38 ± 0.08 |
| Control + cephalexin | 0.31 ± 0.06 |

We claim:

1. A composition of matter comprising an antibody which binds to human influx peptide transporter protein of approximately 120,000 Dalton, wherein said antibody is a monoclonal antibody, F(ab')2, F(ab'), F(ab) or chimeric thereof, said chimeric having a human constant region substituted for a mouse constant region.

2. A composition comprising a monoclonal antibody of claim 1 in admixture with a pharmaceutically acceptable carrier.

3. The monoclonal antibody of claim 1, that is selected from the group consisting of MAb PTC13G6, MAb PTC12D8, and MAb PTC15F11.

4. The monoclonal antibody of claim 2 that is MAb PTC13G6.

5. The monoclonal antibody of claim 2 that is MAB PTC12D8.

6. The monoclonal antibody of claim 2 that is MAB PTC15F11.

7. A composition comprising a monoclonal antibody of claim 3 in admixture with a pharmaceutically acceptable carrier.

8. A composition comprising a monoclonal antibody of claim 4 in admixture with a pharmaceutically acceptable carrier.

9. A method for preparing a monoclonal antibody of claim 1 comprising the steps of:

(a) immunizing an immunocompetent mammal with an immunogen comprising human influx peptide transporter;

(b) fusing lymphocytes of the immunized immunocompetent mammal with myeloma cells to form hybridoma cells;

(c) screening the hybridoma cells of step (b) for influx peptide transporter reactivity;

(d) cloning the influx peptide transporter-reactive hybridoma cells of step (c);

(e) culturing an influx peptide transporter-reactive hybridoma cell in a medium to secrete said monoclonal antibody; and (f) recovering the monoclonal antibody from the culture supernatant.

10. The method of claim 9, wherein said immunocompetent mammal is a mouse.

11. A hybridoma cell that produces a monoclonal antibody of claim 1.

12. A hybridoma cell of claim 9 that is selected from the group consisting of hybridoma PTC13G6, hybridoma PTC12D8, and hybridoma PTC15F11.

13. A process for preparing a hybridoma that produces a monoclonal antibody of claim 9 comprising the steps of:

(a) immunizing an immunocompetent mammal with the human influx peptide transporter;

(b) obtaining lymphocytes from the immunized mammal;

(c) fusing the lymphocytes with myeloma cells; and (d) cloning a hybridoma cell that produces human influx peptide transporter-reactive monoclonal antibodies.

* * * * *